(12) United States Patent
Legay et al.

(10) Patent No.: US 11,344,198 B2
(45) Date of Patent: May 31, 2022

(54) SYSTEM AND METHOD FOR WRITING INTO THE MEMORY OF AN ACTIVE MEDICAL DEVICE IMPLANTABLE BY TELEMETRY

(71) Applicant: SORIN CRM SAS, Clamart (FR)

(72) Inventors: Thierry Legay, Fontenay les Briis (FR); Laure Hery, Maixe (FR)

(73) Assignee: Sorin CRM SAS, Clamart (FR)

( * ) Notice: Subject to any disclaimer, the term of this patent is extended or adjusted under 35 U.S.C. 154(b) by 131 days.

(21) Appl. No.: 16/709,728

(22) Filed: Dec. 10, 2019

(65) Prior Publication Data

US 2020/0178802 A1    Jun. 11, 2020

(30) Foreign Application Priority Data

Dec. 11, 2018 (FR) ........................................ 1872671

(51) Int. Cl.
*A61B 5/00* (2006.01)
*A61N 1/372* (2006.01)

(52) U.S. Cl.
CPC ........ *A61B 5/0031* (2013.01); *A61N 1/37223* (2013.01); *A61N 1/37252* (2013.01); *A61B 2560/045* (2013.01); *A61B 2562/0257* (2013.01)

(58) Field of Classification Search
CPC .............................. A61B 5/0031; A61B 5/686
See application file for complete search history.

(56) References Cited

U.S. PATENT DOCUMENTS

| | | |
|---|---|---|
| 6,510,345 B1 | 1/2003 | Van Bentem |
| 2004/0260363 A1 | 12/2004 | Arx et al. |
| 2005/0113885 A1 | 5/2005 | Haubrich et al. |
| 2005/0204134 A1* | 9/2005 | Von Arx ............ A61N 1/37254 713/168 |
| 2007/0135855 A1 | 6/2007 | Foshee et al. |
| 2008/0044014 A1 | 2/2008 | Corndorf |
| 2010/0076522 A1 | 3/2010 | Hennig et al. |
| 2014/0304773 A1 | 10/2014 | Woods et al. |
| 2015/0089590 A1 | 3/2015 | Krishnan et al. |
| 2018/0309766 A1 | 10/2018 | Marnfeldt |

FOREIGN PATENT DOCUMENTS

| | | |
|---|---|---|
| CN | 104660717 A | 5/2015 |
| JP | 2007-524456 A | 8/2007 |
| JP | 2007-529274 A | 10/2007 |

(Continued)

OTHER PUBLICATIONS

Office Action on EP Application No. 19214154 dated May 8, 2020.

(Continued)

*Primary Examiner* — Michael J D'Abreu
(74) *Attorney, Agent, or Firm* — Foley & Lardner LLP

(57) ABSTRACT

The present invention relates to a system and a method for improving the security of an operation for writing the memory of an active implantable medical device by long distance telemetry, in particular via network connection with a writing main device. The system and method according to the present invention comprise an intermediate proximity device allowing communication between the active implantable medical device and the main writing device and at least one unlocking tool allowing access to the active implantable medical device.

17 Claims, 3 Drawing Sheets

(56) References Cited

FOREIGN PATENT DOCUMENTS

| | | |
|---|---|---|
| JP | 2010-507928 A | 3/2010 |
| WO | WO-2009/023328 A1 | 2/2009 |
| WO | WO-2012/092189 A2 | 7/2012 |

OTHER PUBLICATIONS

Search Report and Written Opinion for French Application No. 1872671 dated Oct. 23, 2019. 10 pages.
Office Action issued in JP Application No. 2019-212179 dated Feb. 22, 2021.
Office Action issued in JP Application No. 2019-212179 dated Dec. 15, 2022.

* cited by examiner

SYSTEM AND METHOD FOR WRITING INTO THE MEMORY OF AN ACTIVE MEDICAL DEVICE IMPLANTABLE BY TELEMETRY

CROSS-REFERENCE TO RELATED APPLICATION

This application claims the benefit of and priority to French Application No. 1872671 filed Dec. 11, 2018, which is incorporated herein by reference in its entirety.

BACKGROUND

The present invention relates to a device, a system and a method for remotely writing into the memory of an implantable active medical device.

An active implantable medical device, for example an implantable pacemaker or a cerebral neurostimulation system, generally comprises a telemetry function allowing communication by non-invasive means with other devices or monitors to transmit information and data from one device to another. Examples of telemetry functions comprise programming of the implantable device to perform certain monitoring or therapeutic tasks, transmission of physiological data acquired in real time by the implantable device and/or updating the program or software of the implantable medical device.

The telemetry communication between the active implantable medical device and another external device can be performed according to a first communication mode, near field telemetry or inductive telemetry. This first mode of communication is based on the inductive coupling between two coils positioned closely facing each other by using the mutual inductance between these coils. This first mode of communication requires an inductive telemetry housing containing a coil and connected via an electrical wire to an external monitor, which housing must be placed and held over the coil of the active implantable medical device to allow communication between both devices by inductance. As a result, the mobility of the patient is reduced during data transfer because the inductive telemetry is in short distance range, of the order of five to ten centimeters, and then requires a close proximity between the device implanted in the patient and the inductive telemetry housing. In addition, inductive telemetry has a slow data transfer rate of the order of several kilobits per second. This transfer rate is not suitable for modern active implantable medical devices, which may contain millions of bits of physiological data of the patient.

For remote monitoring applications, the newest active implantable medical devices use another type of long-range telemetry communication mode, which comprises, for example, wireless telemetry using a network connection (for example the Internet or a telephone line), and telemetry systems using far-field electromagnetic radiation. US 2004/0260363 A1 relates to such long-range telemetry allowing an implantable device to transmit data to a remote monitoring unit and to be programmed by a clinician at a location remote from the patient. For example, long-range telemetry allows clinicians from a hospital to monitor and track patients who have remained at home, or even elsewhere in the world. Long range telemetry thus provides more patient mobility during data transfer, and also provides a higher data transfer rate, which reduces download time.

Nevertheless, for confidentiality and security reasons and in particular in case of hacking of the telemetry system, the use of long-range telemetry is generally limited to downloading the data from the active implantable medical device, for example to perform remote monitoring, and is not applied to the modification or software update of the implantable device, that is to say the writing into the memory of the implantable medical device.

In order to counter the risk of hacking of long-range telemetry between the implantable medical device of the patient and the clinician's external device (for example a control unit), the document US 2004/0260363 A1 cited above suggests to implement a locking and authentication system based on short-range telemetry using the static magnetic field of a magnet to allow remote access to the implantable device and to encrypt long range telemetry communications.

However, concerns about the safety of such a system remain because of the direct access by long-range telemetry between the implantable medical device and an external programming device.

US 2007/0135855 A1 relates to a portable programming device capable of programming a plurality of implantable medical devices jointly or independently, and which is configured to interact simultaneously with a range of external devices, such as a server or a computer. The portable programming device according to US 2007/0135855 A1 functions as a communication channel between the implantable medical devices and an external device via the interface of a network portal, in particular an internet network. When the permission to access the implantable medical device is issued, following the authentication of the identifiers recorded in the portable programming device, downloading and processing data via the portable programming device between each implantable medical device and the external device are allowed.

Nevertheless, the portable programming device according to US 2007/0135855 A1 is limited to clinical use, in particular for large-scale use on several patients simultaneously, and is thus not suitable for home use of a patient who is located away from a medical center.

There is therefore in the field of implantable active medical devices a need to improve the solutions that allow the reprogramming and writing of the memory of such devices by long-range telemetry, in particular by network connection, of a patient being at home by a clinician operating in a medical center several miles from the patient's home.

SUMMARY

Therefore, the object of the present invention is to provide a system and method allowing secure operation of writing memory of an implantable active medical device of a patient being several kilometers away from the clinician performing the writing operation of the memory of the implantable device.

The object of the present invention is achieved by a communication system for enabling a writing operation in the memory of an active implantable medical device. The communication system comprises the active implantable medical device which comprises at least one proximity sensor. The communication system further comprise a remote non-implantable main writing device, an external non-implantable intermediate proximity device which is configured to receive instructions and write data transmitted via the remote main writing device through a network connection, the intermediate proximity device being configured to communicate wirelessly with the implantable medical device, and a first non-implantable external unlocking tool configured to transmit a detectable signal by the proximity sensor when the first unlocking tool is located within a predetermined perimeter of the medical device. The intermediate proximity device is configured to write into the memory of the implantable active medical device according to the instructions transmitted via the remote main writing device in response to a detection of the presence in the predetermined perimeter of the first unlocking tool via the proximity sensor of the active implantable medical device.

As a result, this system makes it possible to improve the security of remote communication with an active implantable medical device thanks to a first safety barrier established by the intermediate device which prevents direct access from the writing device to the implantable medical device by network connection; and a second security barrier with the first unlocking tool that allows access to the implanted medical device when it is located in a perimeter in the immediate vicinity of the implantable medical device. Thus, the writing operation can be done only on the authorization given by the patient who must unlock the active access to its implantable medical device by the use of the first unlocking tool. This makes it possible to improve the security of long-range telemetry by network connection and thus optimize the writing of the memory of an implanted medical device by a writing device of a clinician who is several kilometers away the home of the implanted patient.

The present invention relating to a communication system can be further improved by the following embodiments.

According to one embodiment, the system may further comprise a second unlocking tool configured to allow radiofrequency communication between the active implantable medical device and the intermediate proximity device when the intermediate proximity device has identified the second unlocking tool so that the intermediate proximity device is configured to write into the memory of the active implantable medical device according to the instructions transmitted by the remote main writing device in response to the identification of the second unlocking tool by the intermediate proximity device. The security of the writing operation can thus be further improved thanks to the second unlocking tool that maximizes the number of safety barriers allowing access to the implantable medical device.

According to one embodiment, the second unlocking tool can comprise at least one password entered on the intermediate proximity device, a biometric input received by the intermediate proximity device, a magnetic card read via the intermediate proximity device, a short distance wireless communication which transmits a detectable signal via a proximity sensor of the intermediate proximity device, a magnetic field detected by the intermediate proximity device or a transmission received via a peripheral port of the intermediate proximity device, in particular a USB port. As a result, the second unlocking tool is a proximity unlocking tool for use in the immediate vicinity of the implantable medical device. The second unlocking tool is thus such that its hacking is not possible via long range telemetry for example.

According to one embodiment, the intermediate proximity device may be configured to provide at least one of a visual, audible, or vibrating signal indicating that the writing operation has to be performed. This signaling means makes it possible to alert the patient that a writing operation is to be performed and thus to maximize the chances that a rewriting request is detected by the patient.

According to one embodiment, the intermediate proximity device may be further configured to store the writing data transmitted by the remote main writing device at least until the operation is activated. As a result, the writing data is recorded and kept for at least the time that the writing operation is allowed. This avoids that the instructions and the writing data provided by the clinician to the main writing device are lost while waiting for the identification of the unlocking tool(s).

According to one embodiment, the first unlocking tool may be a permanent magnet or an electromagnet whose static magnetic field is detected by the proximity sensor of the active implantable medical device. The first locking tool is thus easy to manufacture and inexpensive.

According to one embodiment, the non-implantable intermediate proximity device may be a Smartphone, a digital tablet, a connected portable device, a computer, a home medical equipment device or a home automation system.

Thus, the intermediate proximity device is, in particular, a portable device which improves the mobility of the patient during the writing operation from home.

In combination or alternatively, the intermediate proximity device can be used for other purposes than that of the writing operation, thereby reducing the number of devices in the home of a patient.

According to one embodiment, the system may further comprise a portable communication device, in particular to a mobile phone, a tablet, a laptop or a connected watch to which the request for a writing operation is sent via network connection by a message, an SMS ("Short Message Service"), an email or a similar type of alert. Thus, if the request sent to the intermediate proximity device has not been detected by the patient, the sending the request to another device that the patient is likely to keep close to or on her or him increases the probability that the patient answers and authorizes access to its implanted medical device by telemetry to the clinician. Thus, the number of failed attempts for non-response to the request of a writing operation by the clinician can be reduced.

The embodiments may be combined to form more advantageous alternative embodiments of the present invention.

The object of the present invention is also achieved by a method for enabling a writing operation in the memory of an active implantable medical device comprising the steps of sending a network connection request to a wireless non-implantable intermediate proximity device for a writing operation of the implantable active medical device by a remote main writing device, receiving via the intermediate proximity device instructions and writing data sent via network connection by the remote main writing device, placing a first non-implantable external unlocking tool within a predetermined proximity perimeter of the active implantable medical device to allow radiofrequency communication between the intermediate proximity device and the active implantable medical device, and writing said write data into the memory of the active implantable medical device via the intermediate proximity device.

This method allows improving the security of remote communication with an active implantable medical device through a first security barrier established by the intermediate device which prevents direct access of the writing device to the implantable medical device by network connection; and a second security barrier with the first unlocking tool that allows access to the implanted medical device via the intermediate communication device. In addition, the writing operation can be done only on the request of a clinician and the acceptance of this request by a patient who must then allow access to his implantable medical device by the use of the first and the second unlocking tools in the immediate vicinity of the implantable medical device. The succession of these steps makes it possible to further improve the security of exchanges via network connection. Thus, improving the security of long-range telemetry by network connection optimizes the writing of the memory of an implanted medical device by a writing device of a clinician who is several kilometers away the home of the implanted patient.

The present invention relating to a method for enabling a writing operation in the memory of an active implantable medical device can be further improved through the following embodiments.

According to one embodiment, the writing operation of the active implantable medical device can be prevented when the first unlocking tool is not detected by the active implantable medical device, in particular when the distance between the first unlocking tool and the active implantable medical device is larger than 15 centimeters, more particularly larger than 10 centimeters.

As a result, the first unlocking tool requires a very close contact with the active implantable medical device, which may even be in contact with the patient's skin, which implies that the patient is aware of this unlocking step and from which he has supposedly accepted the writing operation request. Hacking of this unlocking operation is thus not possible from long range telemetry.

According to one embodiment, for the method may further comprise receiving, via the intermediate proximity device, the request to authorize radiofrequency communication between the intermediate proximity device and the active medical device implantable by means of a second non-implantable external unlocking tool. The security of the step of the writing operation can thus be further improved thanks to the second unlocking tool that maximizes the number of safety barriers allowing access to the implantable medical device.

According to one embodiment, the second unlocking tool may comprise at least one password entered on the intermediate communication device, a biometric input received the intermediate communication device, a magnetic card read by the intermediate communication device, a short-distance wireless communication which transmits a detectable signal via a proximity sensor of the intermediate communication device, a magnetic field detected by the non-implantable communication device or a transmission received via a peripheral port of the intermediate communication device, in particular a USB port. The use of a second unlocking tool makes it possible to further improve the security of the network connection communication by multiplying the validation requests to authorize the writing operation into the memory of the implantable medical device.

According to one embodiment, the radiofrequency communication between the active implantable medical device and the intermediate communication device can be realized when there is a distance of less than 10 meters between the active implantable medical device and the intermediate communication proximity device.

The distances allowing the communication between the active implantable medical device and the intermediate communication device are thus adapted so that a patient can perform the writing operation at home.

According to one embodiment, the first unlocking tool can emit a signal to the active implantable medical device that comes from an electromagnetic field or a static magnetic field or an inductive field. The first locking tool is thus easy to manufacture and inexpensive.

According to one embodiment, the request for the writing operation can be signaled by a signaling means of the intermediate proximity device, which emits at least one of a visual, audible, or vibrating signal indicating that a writing operation must to be carried out. This signaling means makes it possible to alert the patient that a writing operation is to be performed and thus to maximize the chances of a rewriting request being detected by the patient.

According to one embodiment, the request for a writing operation can also be sent via a network connection to a portable communication device, in particular to a mobile phone, a tablet, a laptop and/or a watch connected via a message, an SMS ("Short Message Service"), an email or any similar type of alert. Thus, if the request sent to the intermediate proximity device has not been detected by the patient, the sending of the request to another device that the patient is likely to keep close to or on her or him increases the probability that the patient answers and authorizes access to its implanted medical device by telemetry to the clinician. Thus, the number of failed attempts for non-response to the request for a writing operation by the clinician can be decreased.

According to one embodiment, the writing data is stored by a storage means of the intermediate proximity device at least until the authorization of a radio frequency communication between the intermediate proximity device and the implantable active medical device. As a result, the writing data is recorded and kept for at least the time that the writing operation is allowed. This thus avoids that the instructions and the writing data provided by the clinician to the main writing device in the previous steps a) and b) are lost while waiting for the identification of the unlocking tool(s).

The embodiments may be combined to form more advantageous alternative embodiments of the present invention.

BRIEF DESCRIPTION OF THE DRAWINGS

The invention and its advantages will be explained in more detail in the following by means of preferred embodiments and relying in particular on the following accompanying figures, wherein.

DETAILED DESCRIPTION

The invention will now be described in more detail using advantageous embodiments in an exemplary method and with reference to the drawings. The described embodiments are merely possible configurations and it should be borne in mind that the individual characteristics as described above can be provided independently of one another or can be omitted altogether during the implementation of the present invention.

Figure 1:
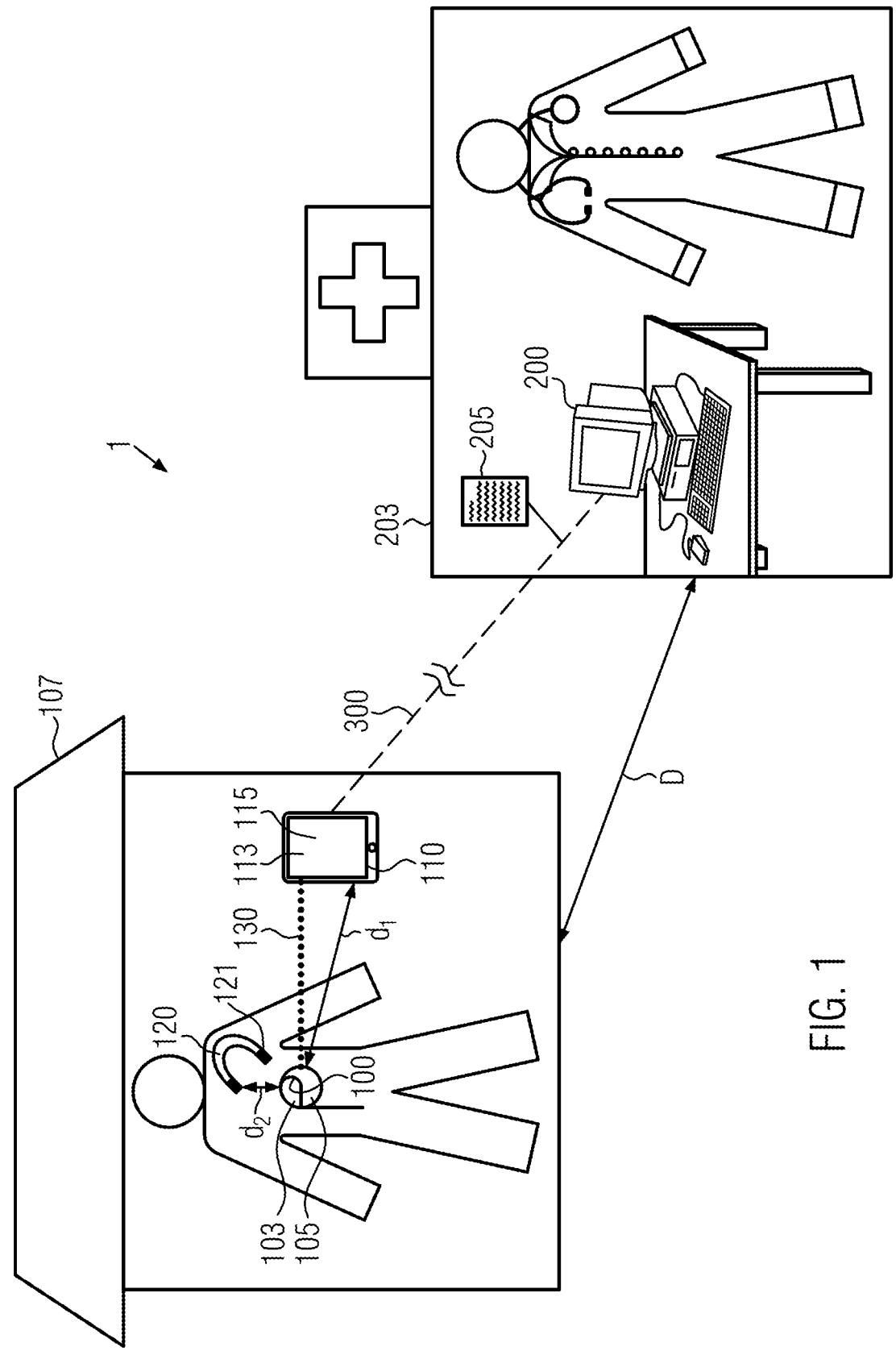
FIG. 1 schematically shows a communication system for enabling a writing operation in the memory of an active implantable medical device according to a first embodiment of the invention.

FIG. 1 schematically illustrates the communication system 1 to enable a writing operation of an active implantable medical device 100 according to a first embodiment of the invention.

The implantable medical device 100, such as an implantable pacemaker or a cerebral neurostimulation system, is configured to be implanted in a patient. The implantable medical device 100 comprises, inter alia, a proximity sensor 103 and a memory 105. Updates of the implantable medical device 100, as well as updates of the implantable medical device software 100, may be required during the life of the patient. In order to prevent the patient from having to go to a hospital center 203 for a clinician to perform a writing operation into the memory 105 of the implantable medical device 100, the communication system 1 is configured to allow a writing operation to be performed into the active implantable medical device 100 from the patient's home 107 by a clinician device 200 located in a hospital center 203 such that the distance D between the active implantable medical device 100 and the clinician device 200 is of several kilometers. To do this, the communication system 1 uses a long range telemetry function.

In order to secure the long range telemetry communication, the communication system 1 also comprises a wireless external non-implantable intermediate proximity device 110. The intermediate proximity device 110 is configured for radiofrequency communication with the implantable medical device 100 at a distance d1 from the implantable medical device 100, such that d1 is less than 10 meters. The intermediate device proximity 110 may be a Smartphone, a digital tablet, a connected portable device, a computer, a home medical equipment device or a home automation system. The intermediate proximity device 110 is therefore suitable for use in the home 107 of a patient. The intermediate proximity device 110 is configured to acquire data transmitted by a clinician device 200, also referred to hereinafter as the main remote writing device 200. The intermediate proximity device 110 is configured to acquire data 205 transmitted by the main writing device 200 via a network connection 300, in particular via a wired or wireless Internet connection, or a telephone line. The intermediate proximity device 110 comprises storage means 113 for storing the writing data 205, at least until authorization to access the implantable medical device 100. In addition, the intermediate proximity device 110 is also configured to receive data from the radiofrequency implantable medical device 100 and transmit it to the main device 200 remotely over a network connection. Thus, the system 1 is configured both for a writing operation into the memory 105 of the implantable medical device 100 but also for the reception of data from the implanted medical device 100 such as for example physiological data acquired by the implanted device 100. This data can be transmitted by the intermediate proximity device 110 to the remote main device 200 which can, for example, adapt the writing operation of the memory 105 of the implantable medical device 100.

According to a preferred embodiment, the main writing device 200 has access to a website, on which a clinician can enter the writing data 205 and such that the intermediate proximity device 110 also has access to this website via an Internet connection and can therefore acquire said writing data 205. According to another embodiment, other types of long-range network connection can be established between the intermediate proximity device 110 and the main writing device 200. Network connection 300 allows communication between the intermediate device proximity 110 and the main writing device 200 over a distance of several kilometers, in particular on the distance D between the home 107 of a patient and a hospital center 203 where the clinician device 200 is located. Thus, the intermediate proximity device 110 connects the implantable medical device 100 and the main writing device 200 without, however, direct communication via the network connection between the main writing device 200 and the implantable medical device 100 to reduce the risk of hacking of the implantable medical device 100.

In addition, in order to alert the patient that a clinician wishes to write or update the software of his implantable medical device 100, the intermediate device proximity 110 of the patient comprises a signaling means which sends a notification, for example in the form of an alert message and/or an audible and/or visual and/or vibrating signal.

To further improve the security of the network connection 300, the communication system 1 comprises a first non-implantable external unlocking tool 120, distinct from the non-implantable wireless intermediate proximity device 110 which is configured to send a detectable signal 121 by the proximity sensor 103 of the implantable medical device 100. According to the embodiment illustrated in FIG. 1, the first unlocking tool 120 is a permanent magnet or an electromagnet whose static magnetic field is detected by the proximity sensor 103 of the active implantable medical device 100. In another embodiment, the first unlocking tool 120 is configured to send a signal 121 from an electromagnetic field, an inductive field, or a human body communication system. When the first unlocking tool 120 is located within a predetermined perimeter, i.e. less than a distance d2 from the medical device 100; such that the distance d2 is less than 15 centimeters, in particular less than 10 centimeters; the presence of the first unlocking tool 120 is detected by the implantable medical device 100. The detection of the presence of the first unlocking tool 120 in the predetermined perimeter allows access of the active implantable medical device 100 to the intermediate proximity device 110. Accordingly, the radio frequency communication 130 between the active implantable medical device 100 and the intermediate proximity device 110 is enabled. The authorization of the radiofrequency communication 130 therefore requires that a patient positions the first unlocking tool 120 close enough to the implantable medical device 100 to unlock it, that is to say less than 15 cm from the implantable medical device 100.

Figure 2:
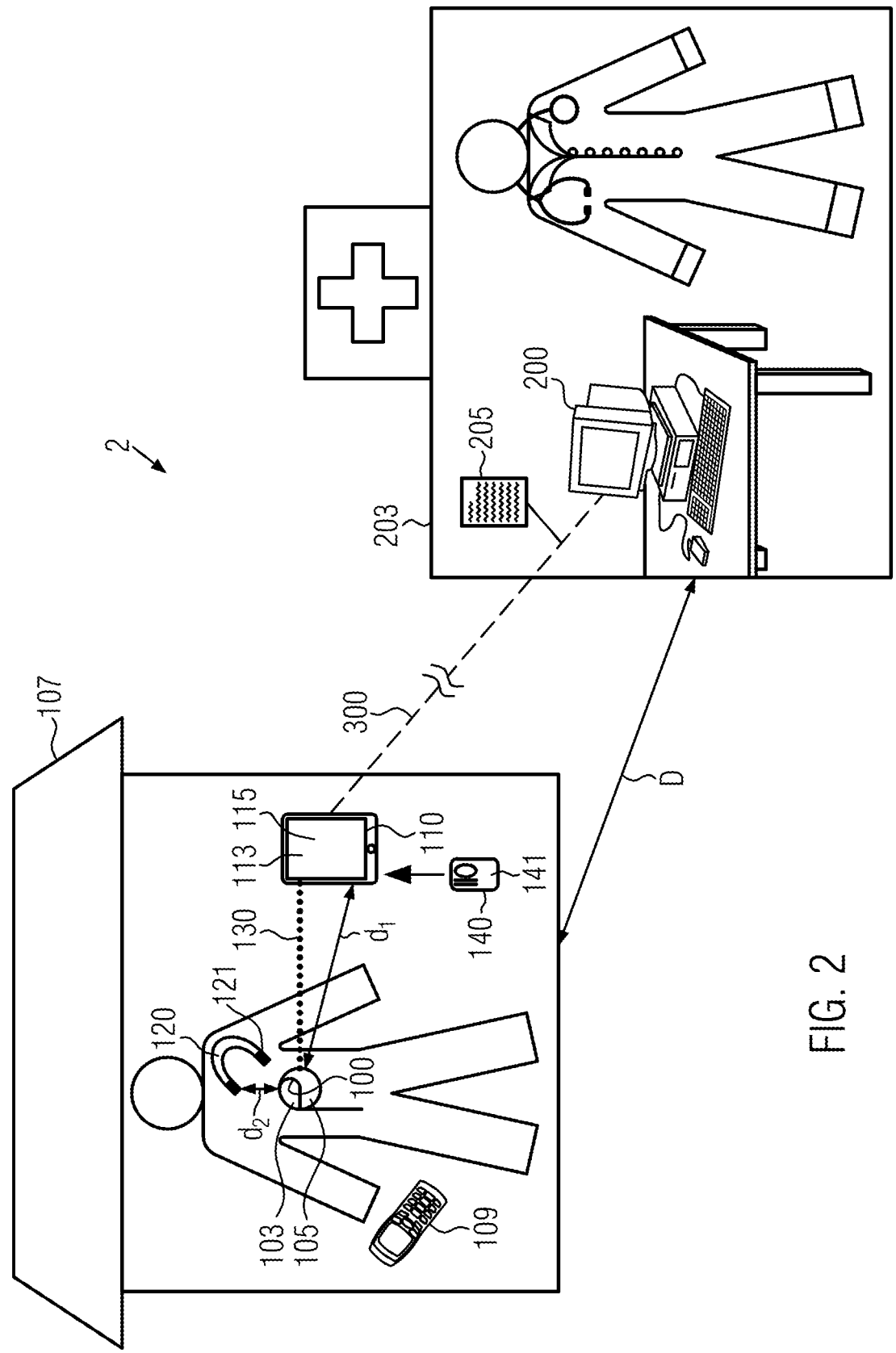
FIG. 2 schematically represents a communication system for enabling a writing operation in the memory of an active implantable medical device according to a second embodiment of the invention.

FIG. 2 schematically illustrates a communication system 2 for enabling a writing operation of an active implantable medical device 100 according to a second embodiment of the invention. Elements with the same numerical references already used for the description of FIG. 1 will not be described again in detail, and reference is made to their descriptions above.

The communication system 2 comprises the active medical implantable device 100, the intermediate proximity device 110, the main writing device 200 and the first unlocking tool 120 as described above for the communication system 1.

In order to further improve the security of the long-range telemetry writing operation, the communication system 2 further comprises a second unlocking tool 140 configured to unlock the intermediate proximity device 110 and thus to allow radio frequency communication between the active implantable medical device 100 and the intermediate proximity device 110.

According to the second embodiment illustrated in FIG. 2, the second unlocking tool 140 is a magnetic card 141 configured to be scanned and read by the intermediate proximity device 110. According to other embodiments, the second unlocking tool 140 may also comprise at least one password to enter the intermediate proximity device 110, a biometric input received by the intermediate proximity device 110, a short-distance wireless communication which transmits a signal detectable by a proximity sensor of the intermediate proximity device 110, a magnetic field detected by the intermediate proximity device 110 or a transmission received via a peripheral port of the intermediate proximity device 110, such as a USB port for example.

Thus, according to the second embodiment, the rewriting authorization in the memory 105 of the active implantable medical device 100 in the system 2 requires that a patient positions the first unlocking tool 120 close enough, that is, say less than 15 cm, from its implantable medical device 100 to unlock it, and that he or she scans his or her personal magnetic card 141 so that the personal magnetic card 141 is read and identified by the intermediate proximity device 110. Therefore, in the second embodiment, the system 2 comprises two proximity unlocking means 120, 140 which are configured to be operated in close proximity to the patient (less than 15 centimeters for the first tool 120) and/or by the patient himself. As a result, these unlocking proximity tools 120, 140 enable to improve and secure a writing operation in the memory 105 of the implantable medical device 100 by long-range telemetry.

This writing operation is signaled to the patient by the signaling means 115 of the intermediate proximity device 110 which issues a notification, for example in the form of an alert message and/or an audible, and/or a visual, and/or a vibrating signal. In addition, according to the second embodiment, a notification can also be sent in parallel to a portable device of the patient 109 such as his mobile phone 109 or a connected watch, to ensure that he is informed of the request for the writing operation, even when he does not have the intermediate proximity device 110 directly at hand. The notification may be at least one visual signal, an audible signal, a vibration, a written message, a voice message at least on the intermediate proximity device 110. The portable device 109 of the patient may receive in parallel a notification of the same or of a different category from that sent to the intermediate proximity device 110.

The operation of the communication system 1 will be explained in the following via the description of the flowchart 500 of FIG. 3. The elements with the same numeral references already used for the description of FIG. 1 will not be described again in detail, and reference is made to their descriptions above.

When an update, a rewriting of the memory 105, an adjustment or a reprogramming of the software of the implantable medical device 100 of the patient is required, a clinician enters a request in the clinician device 200 to notify the patient of a writing operation request. Therefore, in the first step 501 of the method 500 illustrated in FIG. 3, a request is sent from the clinician device 200 via network connection, in particular via an Internet connection, to the patient's intermediate proximity device 110. The reception of this request at the intermediate proximity device 110 is signaled to the patient by the signaling means 115 of the intermediate proximity device 110, which emits an audible notification, a flashing light, a message and/or a vibration.

The first step 501 is followed by the step 502 of acquisition of the writing data 205 by the intermediate proximity device 110. The writing data 205 are input to the main writing device 200 by a clinician. This writing data 205 is transmitted by long-range telemetry to the intermediate proximity device 110. In particular, this writing data 205 is entered on a website and transmitted via an Internet connection to the intermediate proximity device 110 which has also access to this website in order to acquire the writing data 205. The intermediate proximity device 110 comprises a storage means 113 for storing the writing data 205, at least until authorized to access to the implantable medical device 100, i.e., until rewriting in the memory 105 of the implantable medical device 100 has been enabled by the detection of the first unlocking tool 120.

Indeed, the operation of writing into the memory 105 of the implantable medical device 100 requires allowing the intermediate proximity device 110 to transmit to and receive data from the implantable medical device 100.

Figure 3:
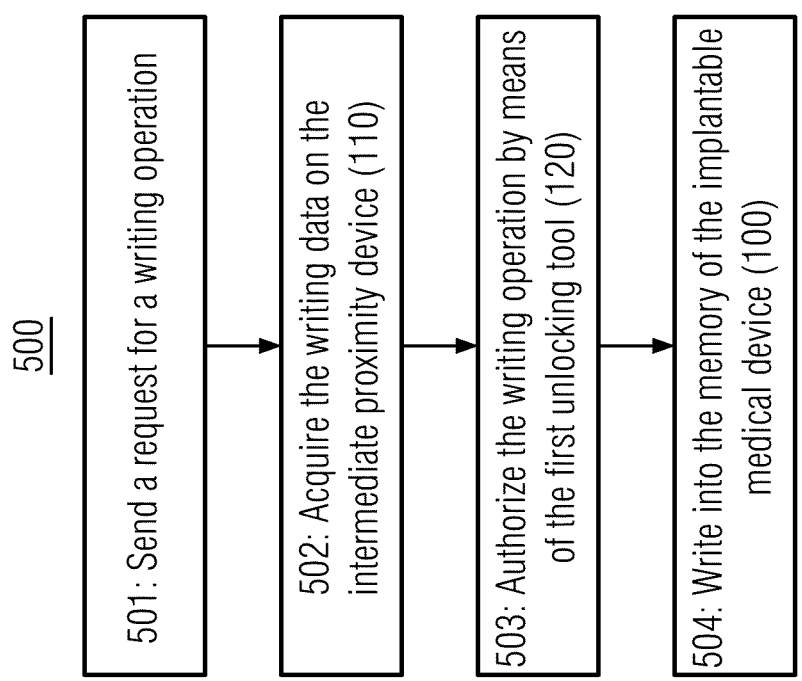
FIG. 3 represents a flowchart of the communication method for enabling a writing operation in the memory of an implantable active medical device according to the first embodiment of the invention.

Therefore, in a second step 503 of the method 500 illustrated in FIG. 3, the first unlocking tool 120 is required to be placed within the predetermined proximity perimeter of the active implantable medical device 100, that is to say less than 10 centimeters, so that the proximity sensor 103 of the implantable medical device 100 detects the presence of the first unlocking tool 120. The detection of the first unlocking tool 120 allows a radiofrequency communication 130 to be enabled between the intermediate proximity device 110 and the active implantable medical device 100. The non-detection of the first unlocking tool 120 by the proximity sensor of the implantable medical device 130 prevents a writing operation of the memory 105 of the implantable medical device 100.

If the unlocking conditions are enabled in step 503, access to the implantable medical device 100 is allowed for the intermediate proximity device 110 for a predetermined period of time. After this predetermined period of time, access to the implantable medical device 100 is locked such that the intermediate proximity device 110 or any other telemetry device can no longer access the implantable medical device 100. According to an advantageous embodiment, the predetermined period of time starts upon receipt by the intermediate proximity device 110 of the request for the writing operation, i.e., at step 501.

In step 504 of method 500, the writing data 205 acquired by the intermediate proximity device 110 is transmitted to the active implantable medical device 100. This results in a writing operation in the memory 105 remote from the implantable medical device 100 according to data 205 entered by the clinician.

When writing to the memory 105 of the implantable medical device 100 or any other reprogramming, updating or adjusting operation of the implantable medical device 100, is successfully performed, the implantable medical device 100 sends an end-of-process notification to the intermediate proximity device 110 that informs the patient that he can remove the first unlocking tool 120 and that transmits the end-of-process notification to the clinician device 200. The clinician device 200, and therefore the clinician himself, is thus informed of the success or failure of the rewriting operation. According to an advantageous embodiment, a predetermined duration of time must be respected between each attempt to rewrite into the implantable medical device 100.

Thus, the method 500 makes it possible to improve the security of the remote communication with the active implantable medical device 100 by means of a first security barrier established by the intermediate proximity device 110 which prevents direct access from the writing device 200 to the implantable medical device 100 via network connection;

and a second safety barrier with the first short-range proximity unlocking tool 120 which allows access to the implanted medical device 100 via the intermediate proximity device 110.

Thus, the writing operation can only be done on the request of the clinician and the acceptance of this request by the patient who must then allow access to his implantable medical device 100 by the use of the first unlocking tool 120 In the immediate vicinity of its implantable medical device 100. The succession of these steps makes it possible to further improve the security of exchanges by network connection.

The operation of the communication system 2 will be explained in the following via the description of the flowchart 600 of FIG. 4. The elements with the same numerical references already used for the description of FIGS. 1, 2 and 3 will not be described again in detail, and reference is made to their descriptions above.

According to the method of the second embodiment, when updating, rewriting the memory 105, adjusting or reprogramming the software of the implantable medical device 100 of the patient is required, a clinician enters a request in the clinician device 200 to notify the patient of a writing operation request. Therefore, in the first step 601 of the method 600 illustrated in FIG. 4, a request is sent from the clinician device via network connection, in particular via an Internet connection, to the patient's intermediate proximity device 110. The reception of this request at the intermediate proximity device 110 is signaled to the patient by the signaling means 115 of the intermediate proximity device 110 which emits an audible notification, a flashing light, a message and/or a vibration. In parallel, according to the second embodiment, a notification, for example a message, an SMS ("Short Message Service"), an email or other, can also be sent to a portable device of the patient 109 such as on his mobile phone 109 or his connected watch. The notification tells the patient the request for a long-range telemetry rewriting operation. The writing operation of the memory 105 of the implantable medical device 100 requires allowing the intermediate proximity device 110 to transmit and receive data to the implantable medical device 100.

The first step 601 is followed by the step 602 of acquiring the writing data 205 by the intermediate proximity device 110. The writing data 205 are input to the main writing device 200 by a clinician. This writing data 205 is transmitted by long-range telemetry to the intermediate proximity device 110. In particular, this writing data 205 is entered on a website and transmitted via an Internet connection to the intermediate proximity device 110 which has also access to this web site to acquire the writing data 205. The writing data 205 is stored by the storage means 113 of the intermediate proximity device 110 at least until authorized to access the implantable medical device 100, i.e. until the rewriting in the memory 105 of the implantable medical device 100 is enabled by the detection of the unlocking tools 120 and 140. Indeed, the operation of writing the memory 105 of the implantable medical device 100 requires allowing the intermediate proximity device 110 to transmit and re receive data from the implantable medical device 100.

Therefore, in a third step 603 of method 600, the authorization of the radio frequency communication 130 between the intermediate proximity device 110 and the active implantable medical device 100 must be authorized by means of the second non-implantable external unlocking tool 140. The non-validation of the second unlocking tool 140 by the implantable medical active device 100 prevents a writing operation in the memory 105 of the implantable medical device 100.

Figure 4:
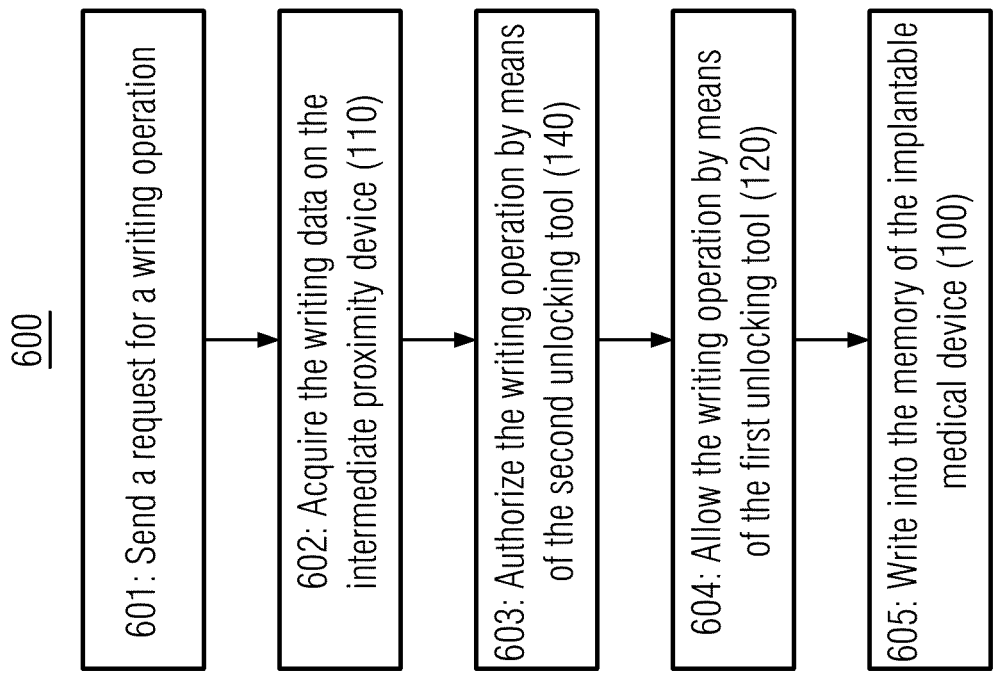
FIG. 4 represents a flowchart of the communication method for enabling a writing operation in the memory of an implantable active medical device according to the second embodiment of the invention.

Then, during a fourth step 604 of the method 600 illustrated in FIG. 4, the first unlocking tool 120 is requested to be placed in the predetermined proximity perimeter of the implantable active medical device 100, that is to say to less than 10 centimeters, so that the proximity sensor 103 of the implantable medical device 100 detects the presence of the first locking tool 103. The detection of the first unlocking tool 103 allows authorizing a radio frequency communication 130 between the intermediate device 110 and the implantable active medical device 100. The non-detection of the first unlocking tool 120 by the proximity sensor of the implantable medical device 130 prevents a writing operation of the memory 105 of the implantable medical device 100.

In a variant which is not illustrated in FIG. 4, step 603 can be performed after step 604. In another variant, steps 603 and 604 can be performed simultaneously.

If the unlocking conditions are enabled in steps 603 and 604, access to the implantable medical device 100 is allowed for the intermediate proximity device 110 for a predetermined period of time. After this predetermined period of time, access to the implantable medical device 100 is locked such that the intermediate proximity device 110 or any other telemetry device can no longer access the implantable medical device 100. Advantageously, the predetermined period of time starts upon reception by the intermediate proximity device 110 of the request for the writing operation, i.e. step 601.

In step 605 of method 600, the writing data 205 acquired by the intermediate proximity device 110 is transmitted to the active implantable medical device 100. This results in a writing operation in the memory 105 remote from the implantable medical device 100 according to the data 205 entered by the clinician.

When writing to the memory 105 of the implantable medical device 100 or any other reprogramming, updating or adjusting operation of the implantable medical device 100, is successfully performed, the implantable medical device 100 sends an end-of-process notification to the intermediate proximity device 110 that informs the patient that it can remove the unlocking tools 120 and 140 and that transmits the end-of-process notification to the clinician device 200. The clinician device 200, and thus the clinician himself or herself, is thus informed of the success or failure of the rewriting operation. According to an advantageous embodiment, a predetermined period of time must be respected between each attempt of rewriting operation of the implantable medical device 100.

Thus, the method 600 makes it possible to improve the security of the remote communication with the implantable active medical device 100 by means of a first security barrier established by the intermediate proximity device 110 which prevents direct access from the writing device 200 to the implantable medical device 100 via network connection; and a second safety barrier by the first short range unlocking tool 120 and the second unlocking tool 140 which allow access to the implanted medical device 100 via the intermediate proximity device 110. Thus, the writing operation can be done only on the request of the clinician and the acceptance of this request by the patient who must then allow access to his implantable medical device 100 by the use of the first 120 and the second unlocking tool 140. The succession of these steps makes it possible to further improve the security of exchanges by network connection.

The systems 1 and 2 and the methods 500 and 600 of the present invention thus make it possible to improve the security of the long range telemetry by network connection and thus to optimize the writing in the memory 105 of the implanted medical device 100 by a writing device 200 of a clinician who is several kilometers away from the home of the implanted patient.

The described embodiments are merely possible configurations and it should be borne in mind that the individual features of the different embodiments may be combined with each other or provided independently of one another.

What is claimed is:

1. A communication system for enabling a writing operation in a memory of an implantable active medical device, the communication system comprising:
   the implantable active medical device which comprises at least one proximity sensor;
   a remote non-implantable main writing device;
   an external non-implantable intermediate proximity device which is configured to receive instructions and writing data transmitted by the remote main writing device through a network connection, the intermediate proximity device configured to communicate wirelessly with the implantable medical device; and
   a first non-implantable external unlocking tool configured to transmit a detectable signal via the proximity sensor when the first unlocking tool is located within a predetermined perimeter of the medical device,
   wherein the intermediate proximity device is configured to write into the memory of the active implantable medical device according to the instructions transmitted via the remote main writing device in response to a detection of the presence in the predetermined perimeter of the first unlocking tool via the proximity sensor of the active implantable medical device.

2. The system of claim 1, further comprising a second unlocking tool configured to allow radiofrequency communication between the medical active implantable device and the intermediate proximity device when the intermediate proximity device has identified the second unlocking tool so that the intermediate proximity device is configured to write into the memory of the active implantable medical device according to the instructions transmitted by the remote main writing device in response to identification of the second unlocking tool by the intermediate proximity device.

3. The system of claim 2, wherein the second unlocking tool comprises at least one password entered on the intermediate proximity device, a biometric input received by the intermediate proximity device, a magnetic card read via the intermediate proximity device, a short distance wireless communication which emits a detectable signal via a proximity sensor of the intermediate proximity device, a magnetic field detected by the intermediate proximity device or a transmission received via a peripheral port of the intermediate proximity device, in particular a USB port.

4. The system of claim 1, wherein the intermediate proximity device is configured to provide at least one of a visual, audible, or vibrating signal indicating that the writing operation has to be performed.

5. The system of claim 1, wherein the intermediate proximity device is further configured to store the writing data transmitted by the remote main writing device at least until the operation is activated.

6. The system of claim 1, wherein the first unlocking tool is a permanent magnet or an electromagnet whose static magnetic field is detected by the proximity sensor of the active implantable medical device.

7. The system of claim 1, wherein the non-implantable intermediate proximity device is a smartphone, a digital tablet, a connected portable device, a computer, a home medical equipment device, or a home automation system.

8. The system of claim 1, further comprising a portable communication device, in particular a mobile phone, a tablet, a laptop, or a connected watch, to which the request for a writing operation is sent via network connection by a message, an SMS ("Short Message Service"), or an email.

9. A method for enabling a writing operation in a memory of an active implantable medical device comprising the steps of:
   sending a network connection request to a wireless non-implantable intermediate proximity device for a writing operation of the active implantable medical device by a remote main writing device;
   receiving via the intermediate proximity device instructions and writing data sent via network connection by the remote main writing device;
   placing a first non-implantable external unlocking tool within a predetermined proximity perimeter of the active implantable medical device to allow radiofrequency communication between the intermediate proximity device and the active implantable medical device; and
   writing said writing data into the memory of the active implantable medical device via the intermediate proximity device.

10. The method of claim 9, further comprising receiving, via the intermediate proximity device, the request to authorize radiofrequency communication between the intermediate proximity device and the active implantable medical device by a second non-implantable external unlocking tool.

11. The method of claim 10, wherein the second unlocking tool comprises at least one of a password entered on the intermediate proximity device, a biometric input received on intermediate proximity device, a magnetic card read by the intermediate proximity device, a short distance wireless communication which transmits a detectable signal via a proximity sensor of the intermediate proximity device, a magnetic field detected by the intermediate proximity device, or a transmission received via a peripheral port of the intermediate proximity device, in particular a USB port.

12. The method of claim 9, wherein the writing operation of the active implantable medical device is prevented when the first unlocking tool is not detected by the active implantable medical device, in particular when the distance between the first unlocking tool and the active implantable medical device is greater than 15 centimeters, more particularly greater than 10 centimeters.

13. The method of claim 9, wherein radiofrequency communication between the active implantable medical device and the intermediate communication proximity device is realized when there is a distance of less than 10 meters between the active implantable medical device and the intermediate communication proximity device.

14. The method of claim 9, wherein the first unlocking tool emits a signal to the active implantable medical device that comes from an electromagnetic field or a static magnetic field or an inductive field.

15. The method of claim 9, wherein the request for the writing operation is signaled by the intermediate proximity device, which emits at least one of a visual, audible, or vibrating signal indicating that the writing operation must be carried out.

16. The method of claim 9, wherein the request for a writing operation is also sent via a network connection to a portable communication device, in particular to a mobile phone, tablet, laptop or watch via a message, an SMS ("Short Message Service"), or an email.

17. The method of claim 9, wherein the writing data is stored by the intermediate proximity device at least until the authorization of a radiofrequency communication between the intermediate proximity device and the implantable active medical device.

\* \* \* \* \*